(12) United States Patent
Choudhary et al.

(10) Patent No.: US 12,121,260 B2
(45) Date of Patent: Oct. 22, 2024

(54) CANNULA FOR PERCUTANEOUS MINIMALLY INVASIVE CANNULATION OF THE VENA CAVA

(71) Applicant: MEDINICE S.A., Warsaw (PL)

(72) Inventors: Sanjeev Choudhary, Warsaw (PL); Piotr Suwalski, Warsaw (PL); Marta Makuch, Warsaw (PL); Jacek Olszewski, Warsaw (PL)

(73) Assignee: MEDINICE S.A., Warsawa (PL)

( * ) Notice: Subject to any disclaimer, the term of this patent is extended or adjusted under 35 U.S.C. 154(b) by 922 days.

(21) Appl. No.: 16/888,715

(22) Filed: May 30, 2020

(65) Prior Publication Data

US 2021/0369301 A1    Dec. 2, 2021

(30) Foreign Application Priority Data

May 28, 2020  (EP) .................................... 20177271

(51) Int. Cl.
*A61B 17/34* (2006.01)
*A61B 17/00* (2006.01)

(52) U.S. Cl.
CPC .... *A61B 17/3423* (2013.01); *A61B 17/00234* (2013.01); *A61B 2017/00243* (2013.01); *A61B 2017/3425* (2013.01); *A61B 2017/3447* (2013.01); *A61B 2017/3486* (2013.01)

(58) Field of Classification Search
CPC .......... A61B 17/3423; A61B 17/00234; A61B 2017/00243; A61B 2017/3425; A61B 2017/3447; A61B 2017/3486; A61B 17/3496; A61B 17/3478; A61B 17/12109; A61B 17/12136; A61B 2017/00331; A61B 2017/22051; A61B 17/3421; A61M 25/0052; A61M 25/007; A61M 25/04; A61M 1/3659; A61M 25/0041; A61M 25/0023; A61M 25/0068; A61M 25/1002; A61M 1/3666; A61M 25/005; A61M 2205/586

See application file for complete search history.

(56) References Cited

U.S. PATENT DOCUMENTS 5,584,803 A * 12/1996 Stevens ................ A61F 2/2433
                                                            604/6.16
6,129,713 A * 10/2000 Mangosong ........ A61M 1/3659
                                                            604/509
2017/0245864 A1 * 8/2017 Franano ........... A61B 17/12109

FOREIGN PATENT DOCUMENTS

WO    9930766 A1    6/1999
WO    0007654 A1    2/2000

* cited by examiner

*Primary Examiner* — Ashley L Fishback
*Assistant Examiner* — Chima U Igboko
(74) *Attorney, Agent, or Firm* — Andrzej Malarz, Esq.

(57) ABSTRACT

A cannula comprising a plastic tube having three longitudinal chambers, including a main chamber, a first lateral chamber and a second lateral chamber, and at least one reinforced section ensuring constant internal diameter, wherein the cannula is equipped from the distal side with a round end narrowing towards the end, in which there are longitudinal holes of a size enabling free venous blood flow, and a balloon. A fragment of the reinforced tube section located below the balloon is bent under an angle α of approximately 90°. From the proximal side, the tube ends with a flexible cone, sealing the cannula tightly, inside which there is a valve closing the main chamber and a port for inflating the balloon connected to the first lateral chamber.

10 Claims, 6 Drawing Sheets

CANNULA FOR PERCUTANEOUS MINIMALLY INVASIVE CANNULATION OF THE VENA CAVA

CROSS REFERENCE TO RELATED APPLICATIONS

This application claims the benefit of European Patent Application No. EP 20177271.2, filed on May 28, 2020, the contents of which are hereby incorporated by reference.

TECHNICAL FIELD

The object of the invention is a cannula for percutaneous minimally invasive cannulation of the vena cava.

BACKGROUND ART

Cardiosurgical operations require releasing the heart from the task of pumping blood, and thus connecting to the patient's bloodstream an artificial lung heart in the extracorporeal circulation system. This device performs mechanical work by generating pressure to allow blood to be pumped through peripheral vessels and oxygenate venous blood. The extracorporeal circulation system is a device with cannulas connected to the main vessels of the heart.

In recent years, minimally invasive methods in which the whole procedure is carried out through a small incision of the skin in the intercostal space, are chosen more often.

The isolation method is crucial for cannulation, i.e. closing the main veins around the cannula so that blood only flows inside the cannula and not through the lumen of the vessel. Closing from the outside by so-called tourniquets is typical for standard surgery, i.e. by sternotomy. However, it can be very difficult or even impossible in minimally invasive surgery, which involves access to the heart and valve under the control of an endoscopic camera using special long tools. Such operations involve a different way of connecting the extracorporeal circulation, a different cannulation site (vein and femoral artery in the groin), and therefore the need for completely different cannulas. Venous cannulas for minimally invasive surgery equipped with a balloon or a special flange in their distal part, which enable the vein to close as effectively as clamping it from the outside, are known. Typically, there are two cannulas, one into the inferior vena cava which is inserted into the femoral vein and the other into the inferior vena cava which is inserted into the jugular vein.

From the description of the invention WO0007654A1 a cannula is known consisting of a curved distal part, an elastic central part and a proximal part. An inflated balloon is mounted on the distal part to facilitate anchoring of the cannula in the vessel. In the central part there is a second, generally cylindrical balloon located peripherally, which increases the diameter of the cannula lumen as a result of pumping. Two ports for inflating both balloons are located in the proximal part. Preferably the curvature of the distal part of the cannula is about 90 degrees.

A cannula used in procedures where temporary cardiac arrest occurs as a result of cardioplegia is known from WO9930766A1. The cannula is placed in the patient's aorta using an extendable cutting blade located at the distal end of the cannula. After making the incision, the blade retracts into the cannula and is then removed from its lumen. At the same time, the sealing balloon located near the cannula outlet opening is pumped. The cannula in its original state is placed in the longitudinal flange after sliding out it adopts the previously given curved shape. The ports used to administer the substance to the aorta or remove blockages from its lumen are at the proximal end.

The cannula equipped externally with a rigid trocar as a guide for placing the cannula in the vessel, is known from U.S. Pat. No. 6,129,713A. The blade for cutting the vessel walls and an inflatable sealing balloon with a protective cover from the blade side is located at the distal end of the trocar. The cannula is pulled out and takes the previously set shape, after placing the trocar in the selected place.

Currently used solutions involve the necessity of tying the cannula and vein to secure a tight, mechanical connection.

SUMMARY

The cannula for percutaneous minimally invasive cannulation of the vena cava which is a plastic tube having at least one conical or round end and equipped with at least one inflow opening that allows blood to enter its interior. The essence of the invention is that the tube having three longitudinal chambers including a main chamber, a first lateral chamber and a second lateral chamber, and at least one reinforced section ensuring constant internal diameter, is equipped from the distal side with a round end narrowing towards the end, in which there are longitudinal holes of a size enabling free venous blood inflow and a balloon. Below the balloon the reinforced section of the tube is located, the fragment of which is bent at an angle $\alpha$ of approximately 90°. The tube is terminated from the proximal side with a flexible cone, sealing the cannula light tightly, inside which there is a valve closing the main chamber and a port for inflating the balloon connected to the first lateral chamber. Inside the second lateral chamber the removable stiffener is located, whose distal end reaches in the most extreme position the base of the balloon, while the proximal end of the stiffener passing through the cone is led out. In the reinforced part, the cannula tube retains shape memory.

Preferably, the longer edge of the holes at the round end coincides with the cannula axis.

In a preferred embodiment, the holes are distributed evenly around the circumference of the round end.

Preferably, the holes are evenly distributed around the perimeter of the round end in two rows and shifted in phase between rows.

In a preferred embodiment, the cannula tube is reinforced with a metal wire solenoid.

In a preferred embodiment, the cannula tube is reinforced with a metal band solenoid.

Preferably, the cannula tube is reinforced with a metal wire mesh of any weave.

Preferably, the two-part integrated needle is mounted inside the round end of the cannula. The needle is composed of a sharp part in the form of a channel and a round part which is located inside the sharp part. The round part has more than one inlet opening and both parts are equipped with separate springs and coupled to the trigger button.

Preferably, the cannula comprises a stylet which runs centrally through the cannula tube, the distal end of stylet reaches the outlet of the round end and the proximal end is led through the cone to the outside and is equipped with an ergonomic handle, which has the form of an ergonomic butterfly.

In a preferred embodiment, the cone is removably connected to the cannula tube.

Advantages

The main advantage of the solution according to the invention is to provide tight protection during minimally invasive cardiac surgery. The cannula can be used in various operating techniques. It is convenient for the operator and significantly reduces the time to prepare the surgical region for surgery. In addition, the use of the cannula either eliminates the need for cutting at all or makes the cut minimal, even smaller than the diameter of the cannula.

The conical end of the cannula allows convenient placement of the cannula inside the vessel and then easy insertion into the next incision. Removing the cone will extend the balloon inflating port, which port is equipped with a short hose.

The design of the cannula allows you to create several versions adapted to different needs, depending on which operating technique will be chosen by the operator, ranging from the simplest and cheapest version to the most equipped version intended for use in more demanding cases.

An important element of the cannula is the stiffener, which allows a straight shape when the cannula enters the vessel. Its removal causes the cannula to return to the state in which part of the reinforced section located below the balloon is curved at an angle of approximately 90°.

BRIEF DESCRIPTION OF THE DRAWINGS

The subject of the invention is presented in the embodiment illustrated by the drawing, where.

DETAILED DESCRIPTION

Figure 1:
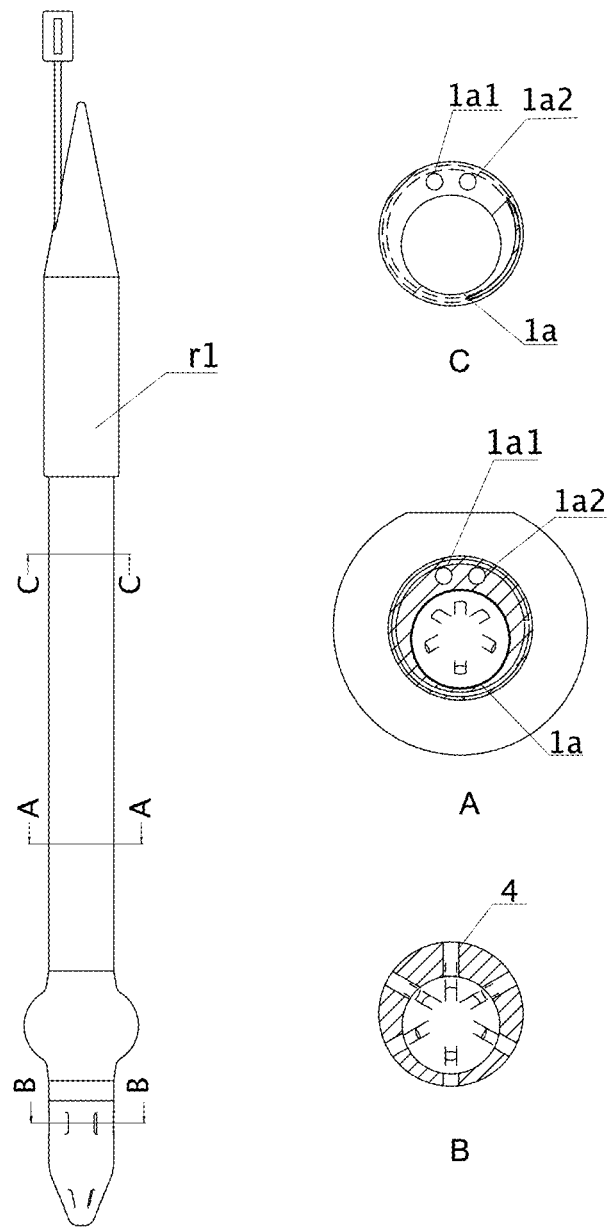
FIG. 1 shows a view of a cannula with one reinforced section with cross-sections A-A, B-B and C-C.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower", "upper", "horizontal," "vertical," "above," "below," "up," "down," "top" and "bottom" as well as derivative thereof (e.g. "horizontally," "downwardly," "upwardly," etc.) should be construed to refer to the orientation as then described or as shown in the drawing under discussion.

There relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both moveable or rigid attachments or relationships, unless expressly described otherwise. Moreover, the features and benefits of the invention are illustrated by reference to the exemplified embodiments.

Accordingly, the invention expressly should not be limited to such exemplary embodiments illustrating some possible non-limited combination of features that may exist alone or in other combination of features; the scope of the invention being defined by the claims appended hereto.

This disclosure describes the best mode or modules of practicing the invention as presently contemplated. This description is not intended to be understood in a limiting sense, but provides an example of the invention presented solely or illustrative purposes by reference to the accompanying drawings to advise one of ordinary skill in the art of the advantages and construction of the invention. In the various views of the drawings, like reference characters designate like or similar parts.

In the first embodiment shown in FIG. 1, the cannula is a flexible tube 1 made of plastic having three longitudinal chambers, a main chamber 1a, a first lateral chamber 1a1 and a second lateral chamber 1a2, and from the distal side a round end 2 in which there are longitudinal holes 4 allowing venous blood to flow freely inside the cannula tube 1. The holes 4 are evenly distributed around the perimeter of the round end 2. Alternatively, the holes 4 can be distributed evenly on the circumference of the round end 2 in two rows and shifted in phase between rows.

Behind the round end 2 there is a soft section m1 bounded from the proximal side with a balloon 6, followed by a reinforced section, the fragment of which is bent at an angle of approximately 90°. The reinforced section then passes into the soft section m2, terminated from the proximal side with the cone 3, sealing the cannula light tightly. Inside the cone 3 there is a port 5 for inflating the balloon 6 and a valve 12 closing the main chamber 1. The inflating port 5 is connected to the first lateral chamber 1a1, through which the filling fluid reaches the balloon 6. The cannula is reinforced with a metal wire solenoid and retains shape memory in the reinforced part. The metal wire can be replaced with tape or mesh. Before placing the cannula in the vessel, a stiffener 8 equipped with ergonomic handle 13 is introduced through the cone 3 into the second lateral chamber 1a2, which forces the tube 1 to take a straight shape. After removing the stiffener 8, the cannula takes the shape consistent with the anatomy and ratio of the angle of entry to the chest.

The cone 3 is connected to the cannula tube 1 detachably so that it can be removed at the right moment and allows access to port 5.

Figures 2A, 2B:
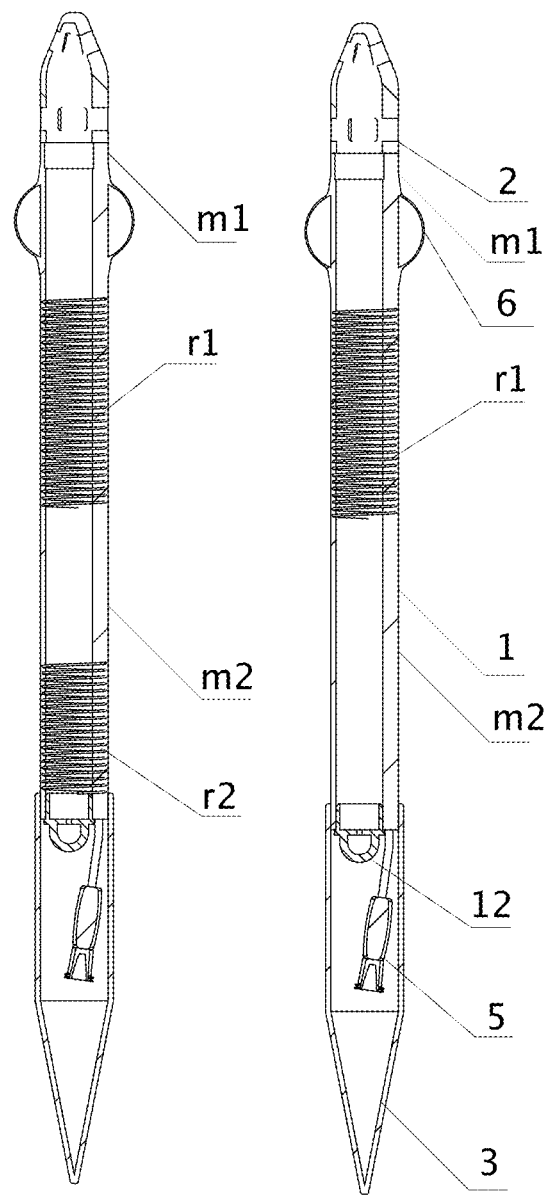
FIG. 2a-shows longitudinal section of the cannula with one reinforced section.
FIG. 2b-shows a longitudinal section of the cannula with two reinforced sections.
Figure 2C:
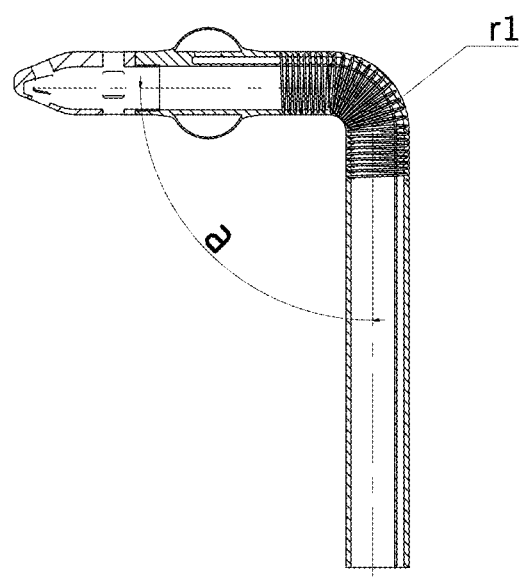
FIG. 2c-shows a longitudinal section of the bent part of the cannula.
Figure 3:
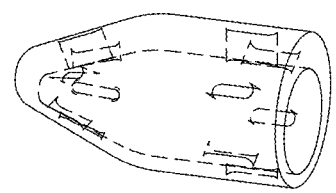
FIG. 3—show isometric views of the round end of the cannula.
Figures 4A, 4B:
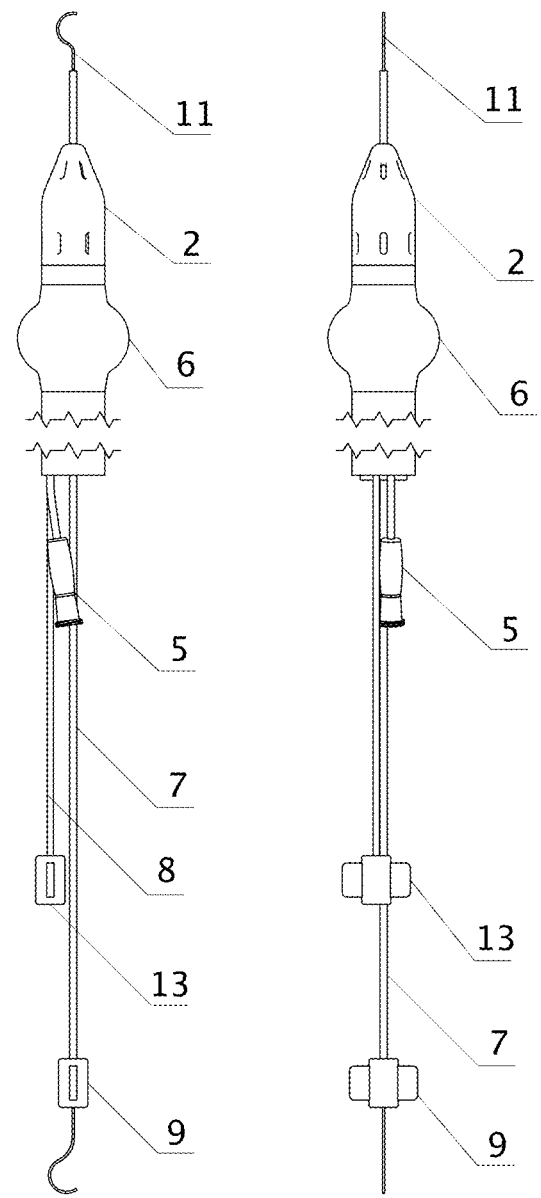
FIG. 4a and FIG. 4b-show views of a cannula with a guide and a stylet.
Figure 5:
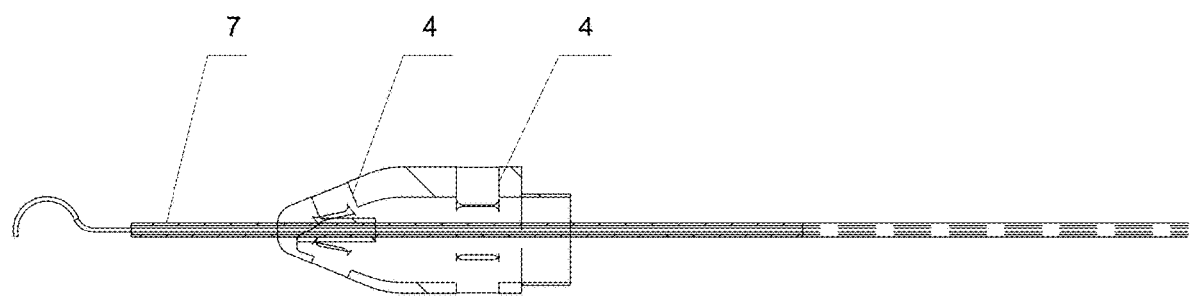
FIG. 5—shows a longitudinal section of the round end of the cannula with a guide and a stylet.

In the second embodiment shown in FIG. 2, the reinforced section of the tube 1 is divided by the soft section m2, on which a clamp is applied. Whereas cone 3 is located at the proximal end of the reinforced section.

The first use of the cannula is that the surgeon, through the incision in the intercostal space gets into the area of the vena cava and the round end 2 is inserted through the incision of the vein into the lumen, after which it is attached using surgical methods. The next step is to remove the stiffener 8 from the second lateral chamber 1a2. Then another incision in the chest wall is made and a surgical tool is inserted into the chest near the operating region, after which the cone 3 is gripped with the tool and leads to a transcutaneous incision in the chest wall, and then cone 3 is pushed out of the body through the percutaneous an incision in the chest so that the surgeon can use a soft cannula with a conical end outside of the patients body. The cone 3 is then removed, thereby releasing port 5, then the balloon 6 is filled with liquid using a syringe. For a soft section m2 of cannula, a clamp is inserted, and the extracorporeal circulation is connected to the cannula end. Then the clamp is removed and blood is already circulating in the closed extracorporeal system. At the end of the procedure, a clamp is applied to the soft section of the cannula, the extracorporeal circulation is disconnected, the fluid is removed from the balloon 6, and after all operations are performed, the cannula is removed.

The use of a cannula using the classic Seldinger method is that a long Seldinger needle is inserted into the vena cava and a guide wire is inserted. Then the guide 11 in a form of flexible wire is threaded through the pin 7 from the round end 2 of the cannula and allows the cannula to be inserted into the vein along the guide 11. When the round end 2 is successfully placed in the vein, blood appears in the cannula. After inserting the appropriate part of the cannula, the stylet 7 and guide wire 11 are being removed through the cone 3. After removing the stylet 7, the blood is in the cannula. After this stage, the next steps are the same as in the first method.

Figure 6:
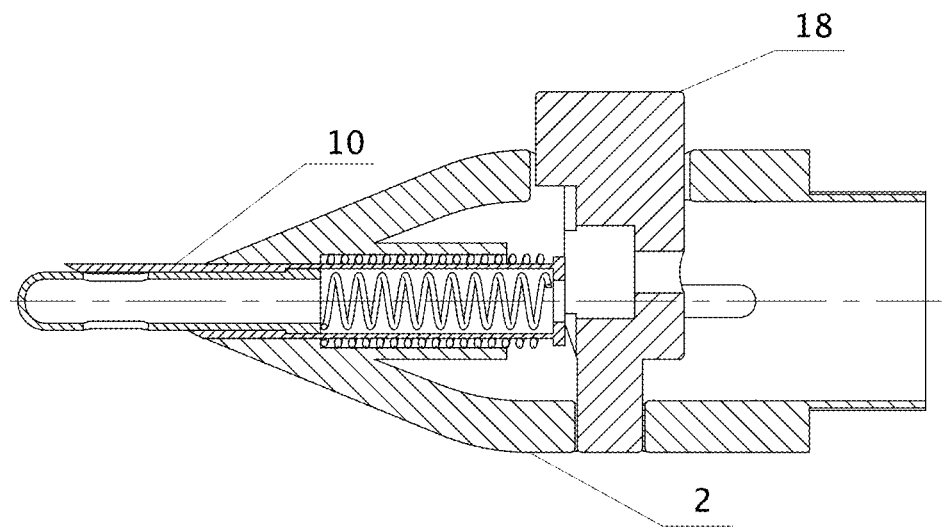
FIG. 6—shows a shows longitudinal section of the round end with an integrated needle.
Figure 7:
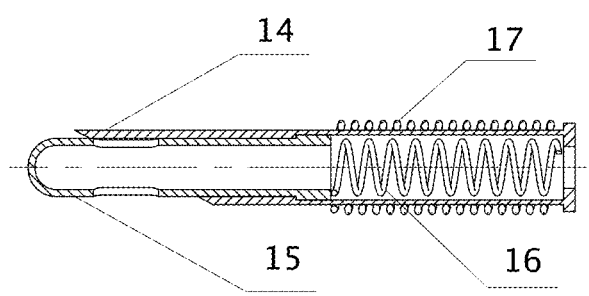
FIG. 7—shows a longitudinal section of the integrated needle.
Figure 8:
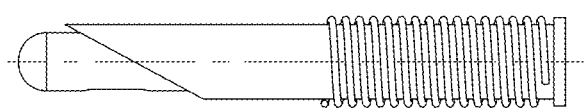
FIG. 8—shows a view of the integrated needle.

Another way to use the cannula is to insert the cannula into the lumen of the vessel without the need for a guide or surgical incision. For this purpose, a cannula equipped with an integrated needle 10 mounted inside the round end 2, as shown in FIG. 6, is used. This needle consists of a sharp part 14 in the form of a channel in which the round part 15 is located, both parts are separate springs 16, 17 and coupled to trigger button 18. The round portion has more than one inlet opening to allow blood to flow quickly into the cannula. The vein is punctured at an appropriate angle with an integrated needle 10. Acting with sufficient force, causes the round needle part 15 of the needle to hide under pressure on the vessel wall. After piercing the vessel wall, the needle round part 15, thanks to the action of the spring 17, extends to secure the blade of the sharp part 14. With the correct angle of attack, the needle 10 is in the lumen of the vein and does not perforate both walls. Blood flows into the cannula and then the trigger button 18 is pressed at the round end 2, causing the needle 10 to hide inside the round end 2, which allows further safe insertion of the cannula to the proper depth while sliding the stiffener 8 out of the second lateral chamber 1a2 to achieve cannula bend according to anatomy.

After removing the pin, the procedure is identical to method 1 and 2.

While the present invention has been described at some length and with some particularity with respect to the several described embodiments, it is not intended that is should be limited to any such particulars or embodiments or any particular embodiment, but it is to be construed with references to be appended claims so as to provide the broadest possible interpretation of such claims in view of the prior art and, therefore, to effectively encompass the intended scope of the invention. Furthermore, the foregoing describes the invention in terms of embodiments foreseen by the inventor for which an enabling description was available, notwithstanding that insubstantial modifications of the invention, not presently foreseen, may nonetheless represent equivalents thereto.

The invention claimed is:

1. A cannula for percutaneous minimally invasive cannulation of the vena cava, comprising
    a plastic tube having at least one conical or round end and equipped with at least one inflow opening allowing blood to enter an interior of the plastic tube wherein the tube comprises three longitudinal chambers, including a main chamber, a first lateral chamber and a second lateral chamber, wherein at least one reinforced tube section ensuring constant internal diameter of the plastic tube, is equipped from the distal side with
    the round narrowed end, in which there are longitudinal holes of a size enabling free venous blood flow, and
    a balloon below which a fragment of
    the reinforced tube section is bent at an angle α, wherein said angle α is 90°, and
    from a proximal side, the tube ends with a flexible cone, sealing the cannula tightly, wherein inside the cone there is
    a valve closing the main chamber and
    a port for inflating the balloon connected to the first lateral chamber, and in addition, inside the second lateral chamber there is
    a removable stiffener, wherein the removable stiffener distal end in a most extreme position reaches a base of the balloon, while a proximal end of the stiffener passing through the cone is led out, and in a reinforced part a cannula tube comprises of a shape memory material.

2. The cannula according to claim 1 characterized in that the longer edge of the holes (4) at the rounded end (2) coincides with a cannula axis.

3. The cannula according to claim 1 wherein a longer edge of holes at the rounded end coincides with a cannula axis wherein in that the holes are evenly distributed along a circumference of the round end.

4. The cannula according to claim 1 wherein the holes are evenly distributed around a perimeter of the round end in two rows and mutually offset in a phase between the rows.

5. The cannula according to claim 1 wherein the cannula tube is reinforced with a metal wire solenoid.

6. The cannula according to claim 1 wherein the cannula tube is reinforced with a metal band solenoid.

7. The cannula according to claim 1 wherein the cannula tube is reinforced with a metal wire mesh of any weave.

8. The cannula according to claim 1 wherein inside the round end of the cannula a two-part integrated needle is mounted, wherein the needle is composed of a sharp part in the form of a channel and a round part located inside the sharp part, wherein the round part has more than one inlet opening and both parts are equipped with separate springs and coupled with a trigger button.

9. The cannula according to claim 1 wherein the cannula comprises further a stylet, wherein the stylet runs centrally through the cannula tube and the distal end of the stylet reaches an outlet of the round end and the proximal end is led through the cone to the outside of the tube, wherein the proximal end of the stylet is equipped with an ergonomic handle, which has the form of an ergonomic butterfly.

10. The cannula according to claim 1 characterized in that the cone is detachably connected to the cannula tube.

* * * * *